(12) United States Patent
Kostuik et al.

(10) Patent No.: US 8,137,405 B2
(45) Date of Patent: Mar. 20, 2012

(54) SPINAL INTERBODY SPACER

(75) Inventors: John Kostuik, Phoenix, AZ (US); Larry McClintock, Gore, VA (US); John I. Williams, Fort Wayne, IN (US)

(73) Assignee: K2M, Inc., Leesburg, VA (US)

( * ) Notice: Subject to any disclaimer, the term of this patent is extended or adjusted under 35 U.S.C. 154(b) by 476 days.

(21) Appl. No.: 12/247,505

(22) Filed: Oct. 8, 2008

(65) Prior Publication Data

US 2010/0087925 A1 Apr. 8, 2010

(51) Int. Cl.
A61F 2/44 (2006.01)

(52) U.S. Cl. ............. 623/17.16; 606/287; 606/288

(58) Field of Classification Search .... 623/17.11–17.16; 606/289–296, 300–331
See application file for complete search history.

(56) References Cited

U.S. PATENT DOCUMENTS

| | | | |
|---|---|---|---|
| 5,053,036 A * | 10/1991 | Perren et al. ............ 606/291 |
| 5,520,690 A | 5/1996 | Errico et al. |
| 5,904,683 A | 5/1999 | Pohndorf et al. |
| 6,099,531 A | 8/2000 | Bonutti |
| 6,342,074 B1 | 1/2002 | Simpson |
| 6,364,880 B1 | 4/2002 | Michelson |
| 6,423,063 B1 | 7/2002 | Bonutti |
| 6,558,423 B1 * | 5/2003 | Michelson ............ 623/17.11 |
| 6,629,998 B1 | 10/2003 | Lin |
| 6,716,214 B1 | 4/2004 | Jackson |
| 6,972,019 B2 | 12/2005 | Michelson |
| 6,984,234 B2 | 1/2006 | Bray |
| 7,001,385 B2 | 2/2006 | Bonutti |
| 7,033,394 B2 | 4/2006 | Michelson |
| 7,041,135 B2 * | 5/2006 | Michelson ............ 623/17.11 |
| 7,077,864 B2 * | 7/2006 | Byrd et al. ............ 623/17.11 |
| 7,175,624 B2 * | 2/2007 | Konieczynski et al. ..... 606/71 |
| 7,318,825 B2 | 1/2008 | Butler et al. |
| 7,651,517 B2 * | 1/2010 | Konieczynski et al. .... 606/305 |
| 2001/0021851 A1 * | 9/2001 | Eberlein et al. ........... 606/69 |
| 2002/0128654 A1 * | 9/2002 | Steger et al. .............. 606/69 |
| 2003/0130737 A1 | 7/2003 | McGahan et al. |
| 2006/0041260 A1 | 2/2006 | Orbay |
| 2006/0149251 A1 | 7/2006 | Ziolo et al. |
| 2007/0073298 A1 | 3/2007 | Beutter et al. |
| 2008/0249624 A1 * | 10/2008 | Josimovic-Alasevic et al. ............ 623/17.16 |
| 2008/0249625 A1 * | 10/2008 | Waugh et al. ........... 623/17.16 |
| 2010/0137919 A1 * | 6/2010 | Wolter ................. 606/308 |

* cited by examiner

Primary Examiner — Eduardo C Robert
Assistant Examiner — Steven Cotroneo
(74) Attorney, Agent, or Firm — Carter, DeLuca, Farrell & Schmidt, LLP

(57) ABSTRACT

A spinal spacer for engagement between vertebrae includes a body extending between a substantially contoured first end surface and a second end surface to define side surfaces and opposing top and bottom vertebral engaging surfaces substantially symmetrical about a centerline axis. At least one opening defines a hollow inner body and includes first and second intersecting openings extending through the top and bottom vertebral engaging surfaces. The second intersecting opening extends through the side surfaces. The second end surface includes at least one aperture formed therethrough in communication with the hollow inner body. A screw opening is defined through at least one plate insert configured to be removably coupled to the second end surface to substantially align the screw opening with the at least one aperture. The bone screw is configured to be threadingly secured within the at least one plate insert.

34 Claims, 10 Drawing Sheets

SPINAL INTERBODY SPACER

BACKGROUND

1. Technical Field

The present disclosure relates to devices for implantation between adjacent vertebrae. Specifically, the disclosure relates to a spinal interbody spacer that inhibits the collapse of the space between adjacent vertebrae after a discectomy.

2. Background of Related Art

After a partial or complete discectomy, the normally occupied space between adjacent vertebral bodies is subject to collapse and/or misalignment due to the absence of all or a part of the intervertebral disc. In such situations, the physician may insert one or more prosthetic spacers between the affected vertebrae to maintain normal disc spacing and/or the normal amount of lordosis in the affected region.

Typically, a prosthetic implant is inserted between the adjacent vertebrae and may include pathways that permit bone growth between the adjacent vertebrae until they are fused together. However, there exists a possibility that conventional prosthetic implants may be dislodged or moved from their desired implantation location due to movement by the patient before sufficient bone growth has occurred.

Therefore, a need exists for a spinal implant that provides a desired amount of lordosis, allows for bone growth between adjacent vertebrae, maintains the space between adjacent vertebrae during bone ingrowth, and resists dislocation from its implantation site.

SUMMARY

According to one embodiment of the present disclosure, a spinal spacer for engagement between vertebrae includes a body having a first end surface at a distal end of the body and a second end surface opposite thereto at a proximal end of the body. The body extends between the first and second end surfaces to define opposing top and bottom vertebral engaging surfaces substantially symmetrical about a centerline axis. The body further defines side surfaces. A hollow inner body is defined by an opening extending through the top and bottom vertebral engaging surfaces. The second end surface of the body includes at least one aperture formed therethrough at an angle relative to the centerline axis and in communication with the hollow inner body. At least one plate insert has a screw opening defined therethrough and is configured to be mounted to the body with the screw opening substantially aligned with the at least one aperture. The plate insert is configured with a lip disposed in the screw opening configured to engage threads of a bone screw to secure the bone screw within the at least one plate insert.

According to another embodiment of the present disclosure, a spinal spacer for engagement between vertebrae includes a body having a first end surface at a distal end of the body and a second end surface opposite thereto at a proximal end of the body. The body extends between the first and second end surfaces to define opposing top and bottom surfaces. The body further defines side surfaces and a hollow open central region extending through the top and bottom vertebral engaging surfaces. The second end surface of the body includes at least one aperture formed therethrough at an angle relative to a centerline axis extending between the proximal and distal surfaces. The at least one aperture has a screw opening defined therethrough. The at least one screw opening has formed therein a lip configured and dimensioned to engage threads on the head of a screw inserted through the at least one aperture.

According to yet another embodiment of the present disclosure, a spinal spacer for engagement between vertebrae includes a body having a first end surface at a distal end of the body and a second end surface opposite thereto at a proximal end of the body. The body extends between the first and second end surfaces to define opposing top and bottom surfaces. The body further defines side surfaces and a hollow open central region extending through the top and bottom vertebral engaging surfaces. The second end surface of the body includes at least one aperture formed therethrough at an angle relative to a centerline axis extending between the proximal and distal surfaces. The at least one aperture has a screw opening defined therethrough and the body further includes a plate cavity. At least one plate insert has a plate screw opening defined therethrough and is configured and dimensioned to be inserted into the plate cavity with the plate screw opening aligned with the body screw opening. The plate screw opening includes a lip configured to engage a bone screw.

The present disclosure also provides for a method of fusing adjacent vertebrae. The method includes inserting a spinal spacer between the surfaces of the adjacent vertebrae. The spinal spacer extends between a first end surface at a distal end and a second end surface at a proximal end to define opposing top and bottom surfaces substantially symmetrical about a centerline axis. The second end surface has at least one angled aperture defined therethrough and at least one corresponding plate insert having a screw opening configured to substantially align with the at least one angled aperture. The method also includes advancing a bone screw through a first angled aperture defined through the second end surface of the spinal spacer at a first angle relative to the centerline axis and into the vertebrae until the bone screw engages bone and threads on the head of the bone screw engage the at least one plate insert to secure the bone screw relative to the spinal spacer.

According to another embodiment of the present disclosure, a method of fusing adjacent vertebrae includes inserting a spinal spacer between the surfaces of the adjacent vertebrae. The spinal spacer extends between a first end surface at a distal end and a second end surface at a proximal end to define opposing top and bottom surfaces substantially symmetrical about a centerline axis. The second end surface of the body includes at least one aperture formed therethrough at an angle relative to a centerline axis extending between the proximal and distal surfaces. The at least one aperture has a screw opening defined therethrough. The method also includes advancing the bone screw through a first aperture defined through the second end surface of the spinal spacer at a first angle relative to the centerline axis and into the vertebrae until the bone screw engages bone and threads on the head of the bone screw engages the at least one screw opening to secure the bone screw relative to the spinal spacer.

BRIEF DESCRIPTION OF THE DRAWINGS

Embodiments of the presently disclosed spinal interbody spacer are described herein with reference to the accompanying drawings, wherein.

DETAILED DESCRIPTION

Figure 1:
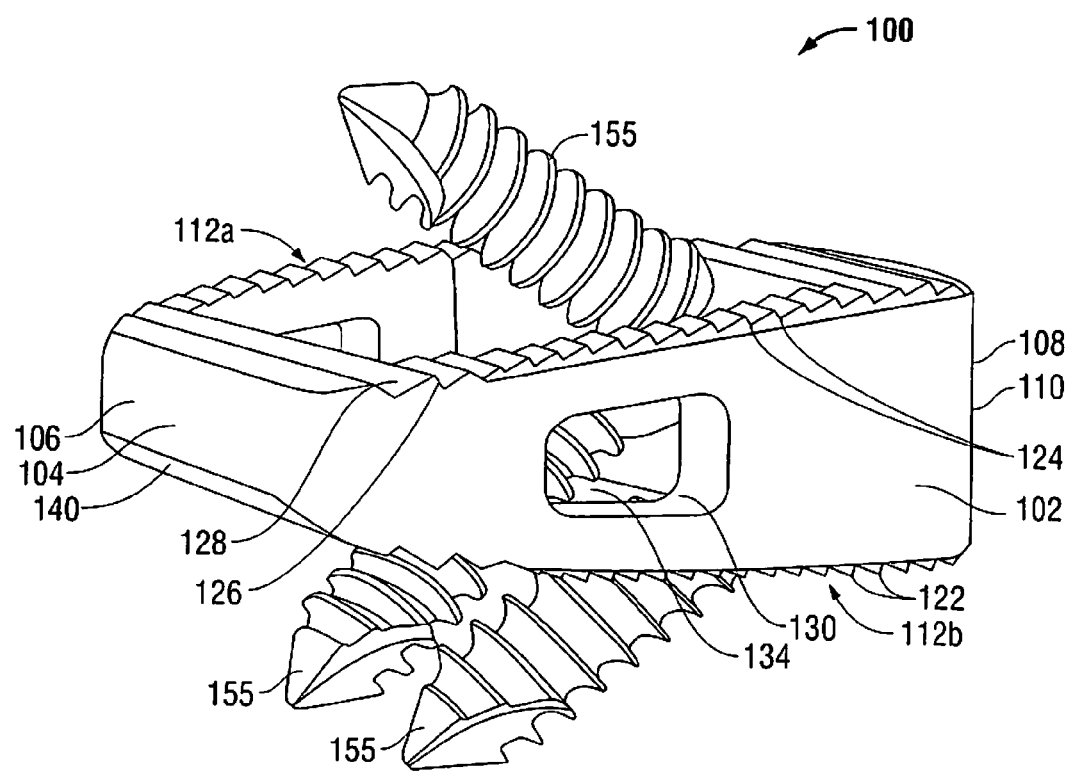
FIG. 1 is a perspective view generally from a leading or distal end of an embodiment of a spinal interbody spacer according to the present disclosure, shown assembled with bone screws.

Embodiments of the presently disclosed spinal interbody spacer will now be described in detail with reference to the drawings, in which like reference numerals designate identical or corresponding elements in each of the several views.

In the drawings and in the description that follows, the term proximal refers to the portion of the device that is closest to the operator, while the term distal refers to the portion of the device that is furthest from the operator. Additionally, in the drawings and in the description that follows, terms such as front, rear, upper, lower, top, bottom, and the similar directional terms are used simply for convenience of description and are not intended to limit the disclosure attached hereto.

Referring now to FIGS. 1-5, there is disclosed an embodiment of a spinal interbody spacer 100 for engagement between vertebrae according to the present disclosure. More particularly, referring to FIGS. 1-3, spinal interbody spacer 100 includes a body 102 having a substantially contoured first end surface 104 at a distal or leading end 106 of the body 102 and a second end surface 108 opposite thereto at a proximal or trailing end 110 of the body 102. The body 102 extends between the first and second end surfaces 104 and 108 to define respective top and bottom vertebral engaging surfaces 112a, 112b, as well as opposed side surfaces 162a, 162b. The top and bottom vertebral engaging surfaces 112a, 112b are disposed opposite to one another.

Figure 2:
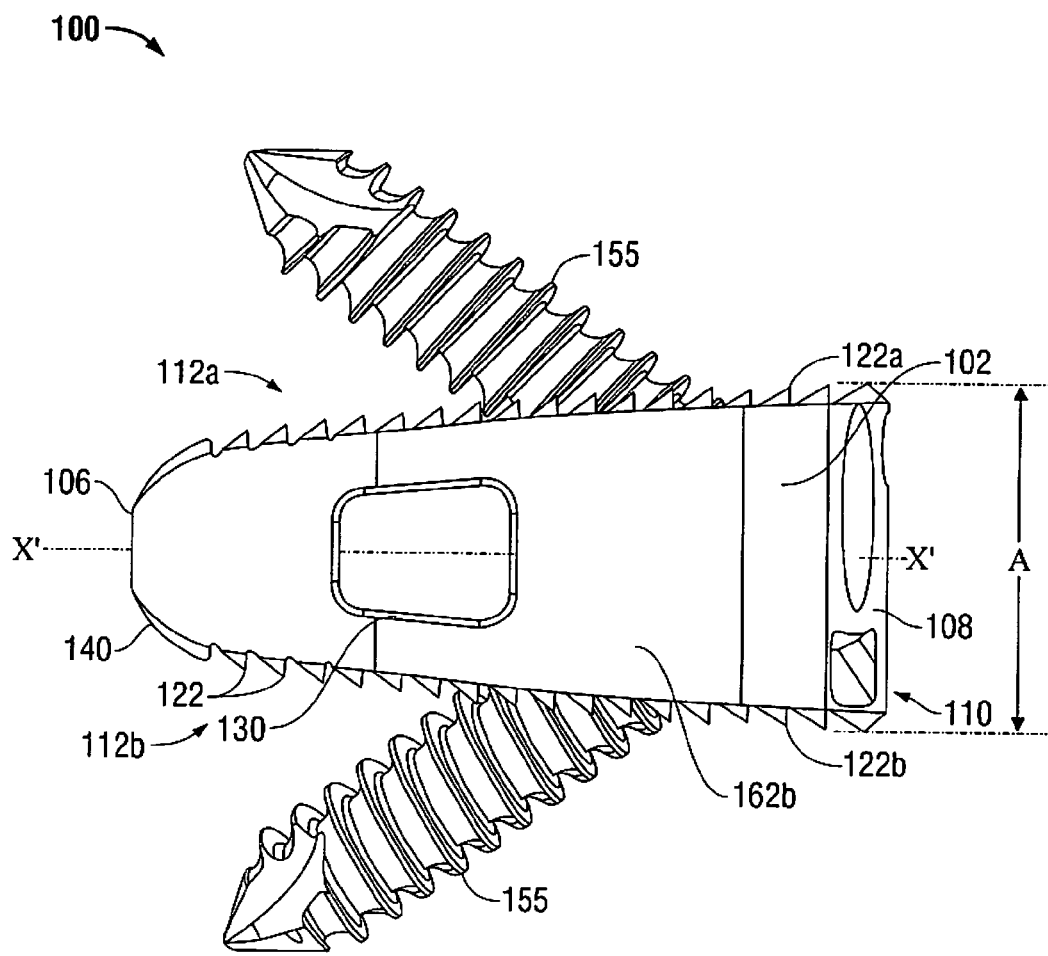
FIG. 2 is a side view of the spinal interbody spacer of FIG. 1.

As best illustrated in FIGS. 1 and 2, the body 102 is configured such that the top and bottom vertebral engaging surfaces 112a, 112b intersect the side surfaces 162a, 162b, respectively, to provide a substantially quadrilateral cross-section with rounded corners 140. As illustrated in FIGS. 1-5, the body 102 has, by way of example, a substantially rectangular cross-section, although other quadrilateral shapes such as a square are also contemplated. In addition, the cross-section shape may also be hexagonal or other suitable multilateral shape. The embodiments are not limited in this context.

Figure 3:
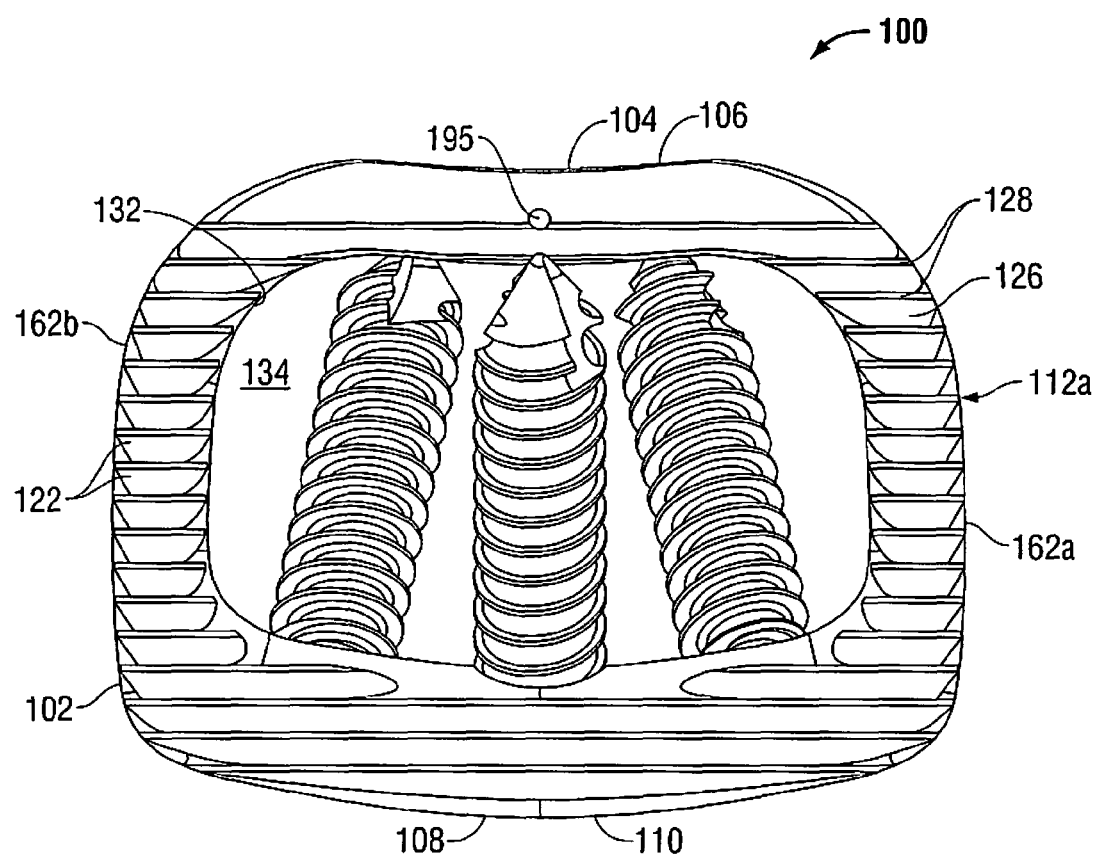
FIG. 3 is top plan view of the spinal interbody spacer of FIG. 1 showing a vertebral-engaging surface.

As best illustrated in FIG. 2, the body 102 is also configured such that the top and bottom vertebral engaging surfaces 112a, 112b have a substantially streamlined convex profile, and are configured to be substantially symmetrical around a centerline axis X-X that extends from the distal end 106 to the proximal end 110. As best illustrated in FIGS. 1 and 3, the body 102 is configured such that the side surfaces 162a, 162b have a substantially atraumatic blunt nose profile with respect to the contoured first end surface 104 and the substantially flat or planar second end surface 108. The intersection of the top and bottom surfaces 112a, 112b of the nose portion with the side surfaces 162a, 162b of the nose may be rounded to enhance the atraumatic character of the nose.

FIG. 3 illustrates a plan view of the top vertebral engaging surface 112a. As illustrated in FIGS. 1-3, surfaces 112a, 112b each have a plurality of protrusions 122 having a particular configuration. The plurality of protrusions 122 define a set of grooves 124 that face towards the proximal end 110. Each groove of the set of grooves 124 has a position along the top and bottom vertebral engaging surfaces 112a, 112b. Each groove of the set of grooves 124 includes a first face 126 that is substantially orthogonal to the top and bottom vertebral engaging surfaces 112a, 112b, i.e., to the axis X-X, at the respective position of the groove. Each groove of the set of grooves 124 includes a second opposing face 128. As best shown in FIG. 1, the second face 128 is substantially sloped or inclined with respect to the top and bottom vertebral engaging surfaces 112a, 112b so that the surfaces 126, 128 converge at the bottom of the groove. The surfaces 126, 128 may directly intersect as shown or a further surface feature, such as a flat surface portion substantially parallel to axis X-X may extend between and connect surfaces 126, 128.

Referring to FIG. 2, it can be seen that the side surfaces 162a, 162b are slightly arcuate such that the apex of the arc thereof has a greater height than both the first and second end surfaces 104 and 108, respectively. As such, the body 102 has a maximum height dimension A as measured by the distance between the tip of a protrusion 122a on the top vertebral engaging surface 112a distanced from the proximal end 110 and the tip of a protrusion 122b on the bottom vertebral engaging surface 112b correspondingly distanced from the proximal end 110.

Referring again to FIGS. 1 and 2, the body 102 may further include an aperture 130 formed therein that extends transversely across the body 102 through the side surfaces 162a, 162b. The aperture 130 may be disposed transversely under at least a portion of the top vertebral engaging surface 112a and over at least a portion of the bottom vertebral engaging surface 112b.

Referring again to FIGS. 1 and 3, the body 102 may further include an aperture 132 formed therein that may extend vertically through the body 102. The paths of the apertures 130, 132 intersect to form a hollow central region 134 (FIG. 3) of the body 102. The apertures 130, 132 and the hollow central region 134 may be filled with osteoconductive or osteoinductive materials (e.g. bone, bone chips, bone substitutes, bone growth promoting materials such as bone morphogenic proteins, etc.), or both, to enable and/or promote growth of vertebral bone therebetween to promote fusion of the adjacent spine segments and/or anchor the spinal interbody spacer 100 within the spine of a patient.

As best shown in FIG. 3, the top vertebral engaging surface 112a includes at least one aperture 195 formed therein and at least partially penetrating therethrough configured to receive an optional fiduciary insert (not shown), thus allowing the orientation of the spinal interbody spacer 100 to be determined using a number of different imaging modalities as are known in the art. This feature is particularly important when spacer 100 is made from a substantially radiolucent material (e.g. polyetheretherketone or PEEK). In embodiments, top and bottom vertebral engaging surfaces 112a, 112b may include additional apertures (not shown) at least partially penetrating therethrough to complement aperture 195.

Figure 4:
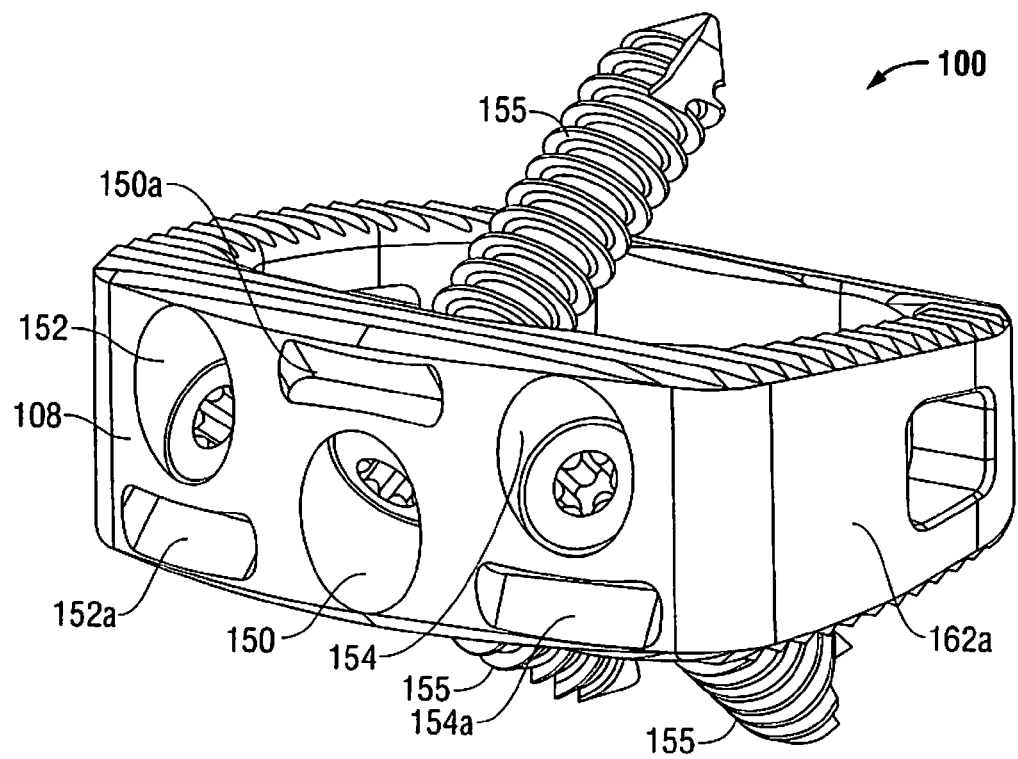
FIG. 4 is a rear elevational view of the trailing or proximal end of the spinal interbody spacer of FIG. 1.
Figure 5:
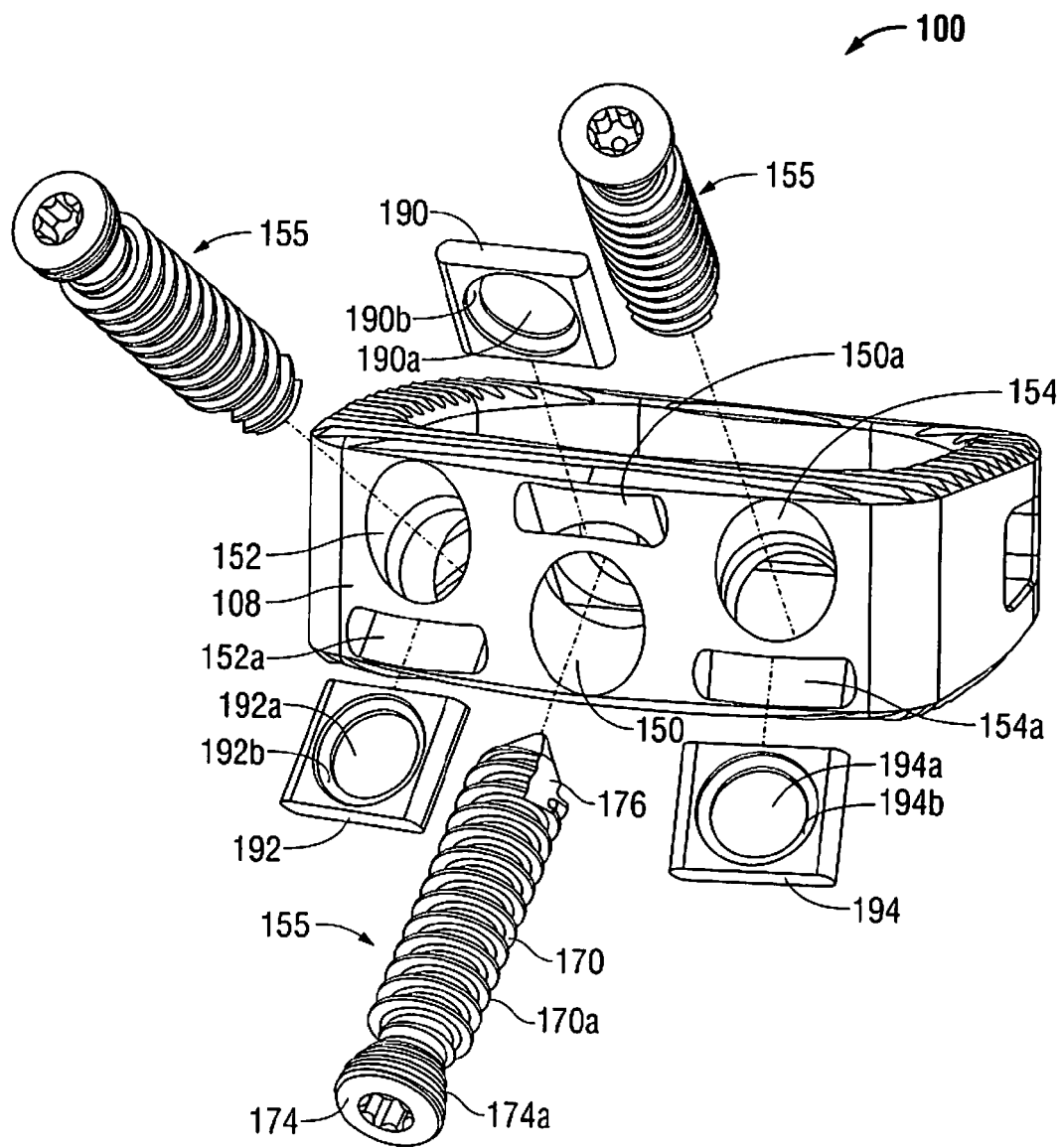
FIG. 5 is an exploded rear elevational view of the trailing or proximal end of the spinal interbody spacer of FIG. 1 with parts separated.

Referring to FIGS. 4 and 5, the proximal end 110 of the body 102 further includes a plurality of angled apertures disposed through the second end surface 108 communicating with the hollow central region 134. In the illustrated embodiment, three apertures are disposed through the second end surface 108, including one aperture 150 angled in a first direction, and two apertures 152 and 154 having a corresponding degree of angle in a second direction. In use of the spinal interbody spacer 100, the body 102 may be inverted such that aperture 150 is angled in the second direction and apertures 152, 154 are angled in the first direction. Each of angled apertures 150, 152, 154 are adapted to receive a bone screw 155 therethrough for insertion into bone, as will be discussed in further detail below.

Referring to FIGS. 4 and 5, the proximal end 110 of the body 102 further includes a plurality of insert slots 150a, 152a, 154a defined in the second end surface 108 communicating with angled apertures 150, 152, 154, respectively. As shown in FIG. 5, each of slots 150a, 152a, 154a are configured and dimensioned to slidably receive a respective plate insert 190, 192, 194 therein. Each of plate inserts 190, 192, 194 includes a respective screw opening 190a, 192a, 194a defined therethrough and an annular sidewall extending downward from a top surface of plate inserts 190, 192, 194 to form a corresponding lip 190b, 192b, 194b proximate a bottom surface thereof. When plate inserts 190, 192, 194 are inserted within slots 150a, 152a, 154a, screw openings 190a, 192a, 194a substantially align with corresponding apertures 150, 152, and 154 or are otherwise coincident therewith to permit the bone screw 155 to be advanced therethrough. As bone screw 155 is advanced through any one of apertures 150, 152, 154 to communicate with hollow central region 134, bone screw 155 threadingly engages lips 190b, 192b, 194b to retain bone screw 155 within plate inserts 190, 192, 194, as will be discussed in further detail below. Plate inserts 190, 192, 194 are constructed of medical grade titanium. Further, the surface of plate inserts 190, 192, 194 may be anodized to provide a porous coating for absorbing a colored dye and/or to provide corrosion resistance.

Figure 6:
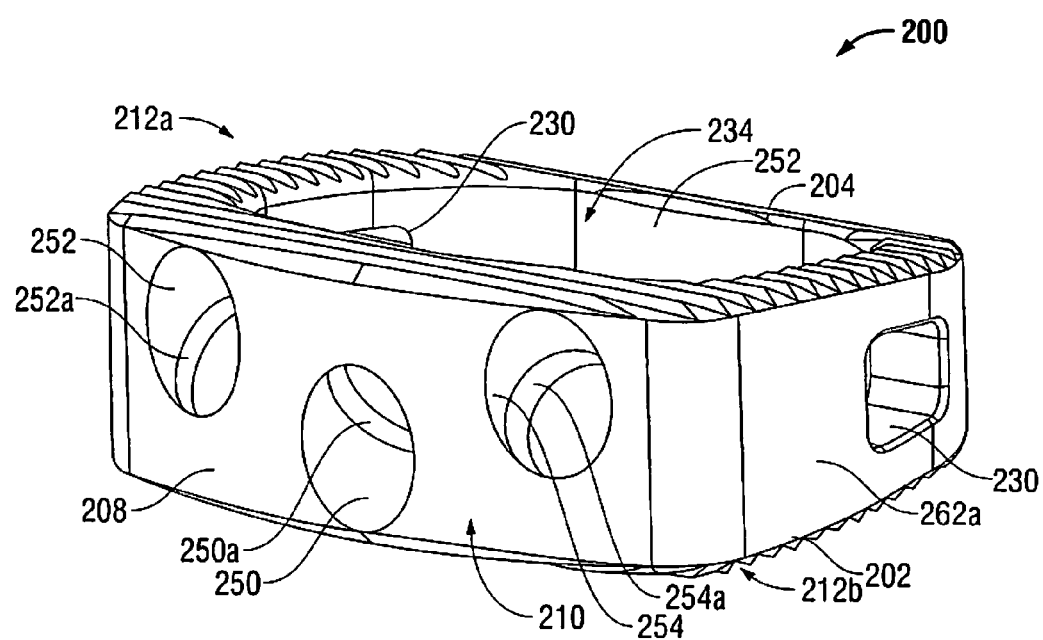
FIG. 6 is a rear elevational view of a trailing or proximal end of a spinal interbody spacer according to an embodiment of the present disclosure.

Referring now to FIG. 6, a spinal interbody spacer 200 is shown according to another embodiment of the present disclosure. Spinal interbody spacer 200 is substantially as described above with respect to spacer 100 but includes features distinct from spacer 100 which will be discussed in detail below. Spacer 200 is constructed of medical grade titanium. Further, the surface of spacer 200 may be anodized to provide a porous coating for absorbing a colored dye and/or to provide corrosion resistance. As with spacer 100, spacer 200 includes a body 202 extending between a first end surface 204 and a second end surface 208 to define respective top and bottom vertebral engaging surfaces 212a, 212b, as well as opposed side surfaces 262a, 262b. An aperture 230 through the side surfaces 262a, 262b extends transversely across the body 202 to intersect an aperture 232 extending vertically through body 202 to form a hollow central region 234. These elements function substantially as described above with respect to spacer 100 and will not be discussed in further detail herein.

Body 202 further includes a plurality of angled apertures 250, 252, 254 disposed through the second end surface 208 communicating with the hollow central region 234. In the illustrated embodiment, three apertures 250, 252, 254 are disposed through the second end surface 208, including one aperture 250 angled in a first direction, and two apertures 252 and 254 having a corresponding degree of angle in a second direction. Each of angled apertures 250, 252, 254 are adapted to receive a bone screw 155 therethrough for insertion into bone, as will be discussed in further detail below. Each angled aperture 250, 252, 254 includes an annular sidewall extending outward from a side surface thereof to form a corresponding lip 250a, 252a, 254a proximate a bottom surface of each angled aperture 250, 252, 254 and distal a top surface of each angled aperture 250, 252, 254. As a bone screw is advanced through any one of apertures 250, 252, 254 to communicate with hollow central region 234, the bone screw threadingly engages lips 250a, 252a, 254a to retain the bone screw within apertures 250, 252, 254, as will be discussed in further detail below.

Figure 7A:
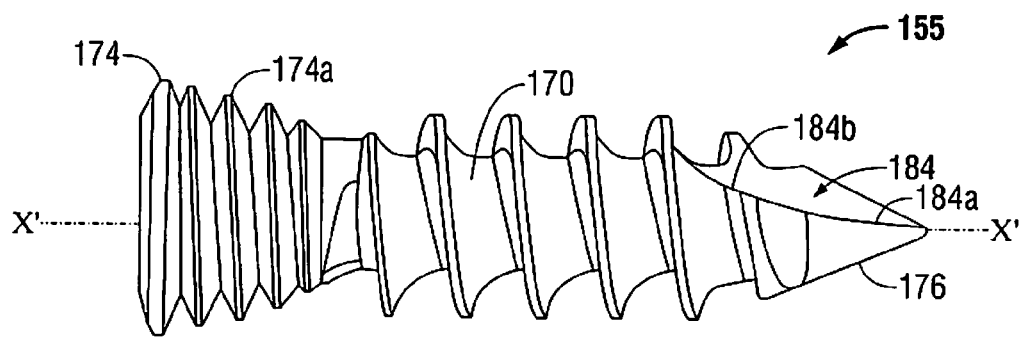
FIGS. 7A and 7B are side views of a bone screw for use with the spinal interbody spacers of FIGS. 1 and 6 according to an embodiment of the present disclosure.
Figure 7B:
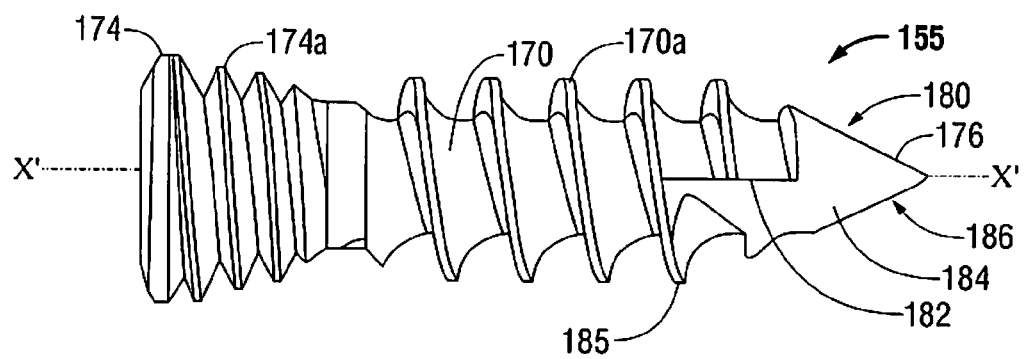

Referring now to FIGS. 7A and 7B, one embodiment of bone screw is shown referenced generally as 155. As described herein, bone screw 155 is configured for use with spinal interbody spacer 100 and/or spinal interbody spacer 200. Bone screw 155 includes a shank 170, a tapered head portion 174 at a proximal end of the shank 170, and a pointed tip portion 176 at a distal end of the shank 170. The shank 170 has a uniform outer diameter and a first continuous helical thread 170a formed thereon for threaded insertion into bone. A second continuous helical thread 174a is formed on the head portion 174 for engaging the lip of the corresponding screw openings 190a, 192a, 194a. The pitch of the first thread 170a is greater than the pitch of the second thread 174a. Each of the first and second threads 170a, 174a has a substantially uniform pitch.

Bone screw 155 further includes a self-starting portion 180 that extends proximally from the pointed tip portion 176. The self-starting portion 180 includes first and second sidewalls 182, 184 that define a flute section 186. As best shown in FIG. 7B by way of example, the first and second sidewalls 182, 184 of the flute section 186 extend from the pointed tip portion 176 to a crest 185 of thread 170a near the distal end of shank 170. The first sidewall 182 is planar and is aligned along a central longitudinal axis X'-X' of the bone screw 155 such that first sidewall 182 is coplanar with the central longitudinal axis X'-X'. As best shown in FIG. 7A by way of example, the second sidewall 184 further includes a planar portion 184a that is parallel to the central longitudinal axis X'-X' and an arcuate portion 184b that extends proximally from the planar portion 184a. The arcuate portion 184b is cut along a radius of curvature, as shown in FIG. 7A. Preferably, bone screws 155 are constructed of a material which is harder than the material of plate inserts 190, 192, 194 (FIG. 5) and/or lips 250a, 252a, 254a (FIG. 6). For example, the bone screw may be made of titanium alloy (e.g., Ti-6Al-4V) with the plate inserts and/or lips made of a softer compatible material, such as a softer titanium material.

In use with spacer 100, bone screw 155 is advanced (i.e., rotated clock-wise) through apertures 150, 152, 154 toward hollow central region 134 such that self-starting portion 180 engages vertebral bone to threadingly advance thread 170a of shank 170 therein. Since the titanium makeup of plate inserts 190, 192, 194 is softer than the titanium alloy makeup of the bone screw 155, as bone screw 155 is advanced through any one of apertures 150, 152, 154 toward hollow central region 134, thread 174a of head portion 174 engages the corresponding lip 190b, 192b or 194b to deform the lip and secure bone screw 155 in the corresponding screw opening 190a, 192a or 194a such that bone screw 155 resists backing out of the screw opening. Further, head portion 174 of bone screw 155 is dimensioned to engage lips 190b, 192b, 194b to prevent further advancement of bone screw 155 toward hollow central region 134. This type of screw locking arrangement is disclosed and shown in U.S. Pat. No. 6,322,562 to Wolter, the entire contents of which are hereby incorporated by reference as if repeated herein.

With reference to use with spacer 200, the titanium makeup of lips 250a, 252a, 254a is softer than the titanium alloy makeup of the bone screw 155, as bone screw 155 is advanced through any one of apertures 250, 252, 254 toward hollow central region 234, thread 174a of head portion 174 engages the corresponding lip 150a, 152a, or 154a to deform the lip and secure bone screw 155 in the corresponding aperture 150, 152, 154 such that bone screw 155 resists backing out of the aperture. Further, head portion 174 of bone screw 155 is dimensioned to engage lips 150a, 152a, or 154a to prevent further advancement of bone screw 155 toward hollow central region 234.

Figure 8A:
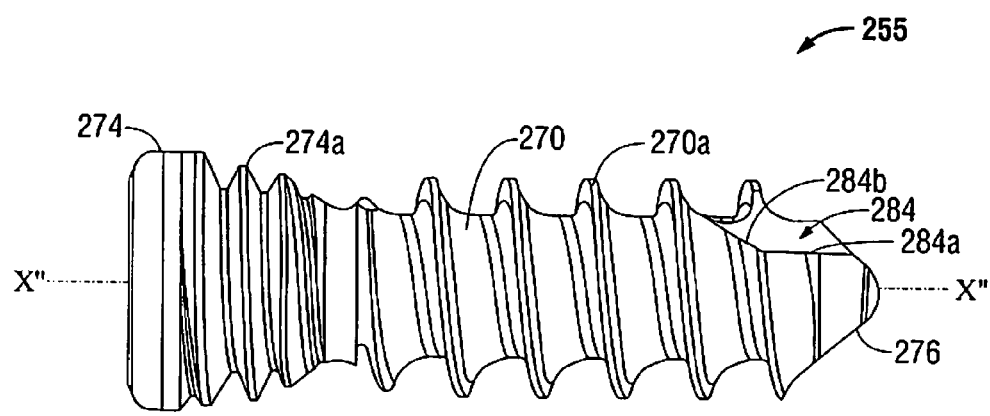
FIGS. 8A and 8B are side views of a bone screw for use with the spinal interbody spacers of FIGS. 1 and 6 according to another embodiment of the present disclosure.
Figure 8B:
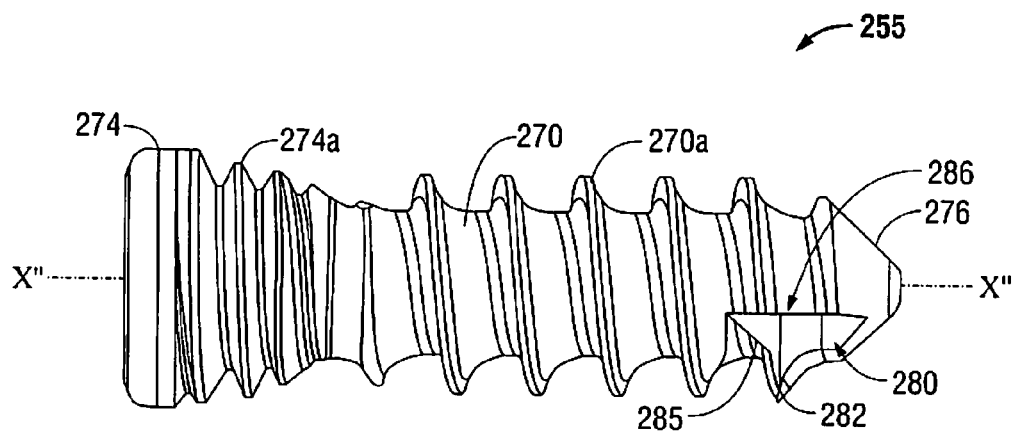

Referring now to FIGS. 8A and 8B, another embodiment of a bone screw is shown referenced generally as 255. As described above with reference to bone screw 155, bone screw 255 is configured for use with spinal interbody spacer 100 and/or spinal interbody spacer 200 in the same manner as described hereinabove. Bone screw 255 includes a shank 270, a tapered head portion 174 at a proximal end of the shank 270, and a rounded tip portion 276 at a distal end of the shank 270. The shank 270 has a uniform outer diameter and a first continuous helical thread 270a formed thereon for threaded insertion into bone. A second continuous helical thread 274a is formed on the head portion 274 for engaging lips 190b, 192b, 194b (FIG. 5) or lips 150a, 152a, 154a (FIG. 6). The pitch of the first thread 270a is greater than the pitch of the second thread 274a. Each of the threads 270a, 274a has a substantially uniform pitch.

Bone screw 255 further includes a self-tapping portion 280 that extends proximally from the rounded tip portion 276. The self-tapping portion 280 includes first and second sidewalls 282, 284 that define a flute section 286. The first and second sidewalls 282, 284 of the flute section 286 extend from the rounded tip portion 276 to a crest 285 of thread 270a near the distal end of shank 270. The first sidewall 282 is planar and is parallel to a central longitudinal axis X"-X" of the bone screw 255 such that first sidewall 282 is offset from the central longitudinal axis X"-X". As best shown in FIG. 8A by way of example, the second sidewall 284 further includes a planar portion 284a that is parallel to the central longitudinal axis X"-X" and an arcuate portion 284b that extends proximally from the planar portion 284a. The arcuate portion 284b is cut along a radius of curvature, as shown in FIG. 8A. Preferably, bone screws 255 are constructed of a material which is harder than the material of plate inserts 190b, 192b or 194b (FIG. 5) and/or lips 150a, 152a, 154a (FIG. 6). For example, the bone screws may be made of titanium alloy (e.g., Ti-6Al-4V) with the plate inserts and/or lips made of a softer compatible material, such as a softer titanium material.

Figure 9A:
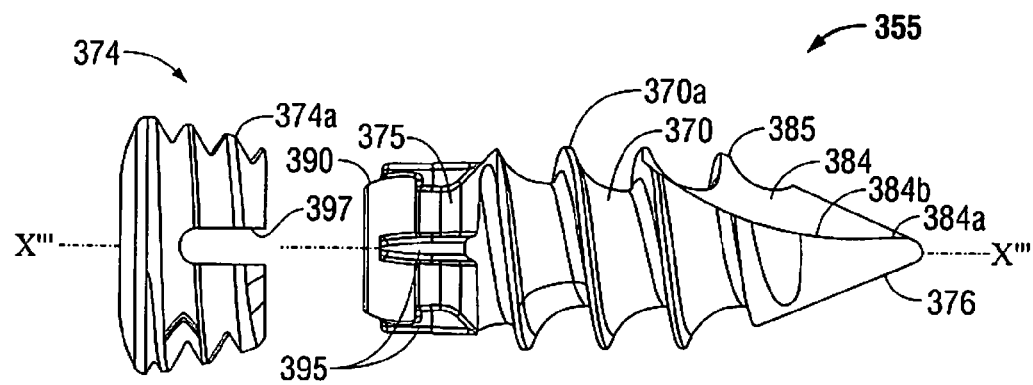
FIGS. 9A and 9B are side views of a bone screw for use with the spinal interbody spacers of FIGS. 1 and 6 according to another embodiment of the present disclosure.
Figure 9B:
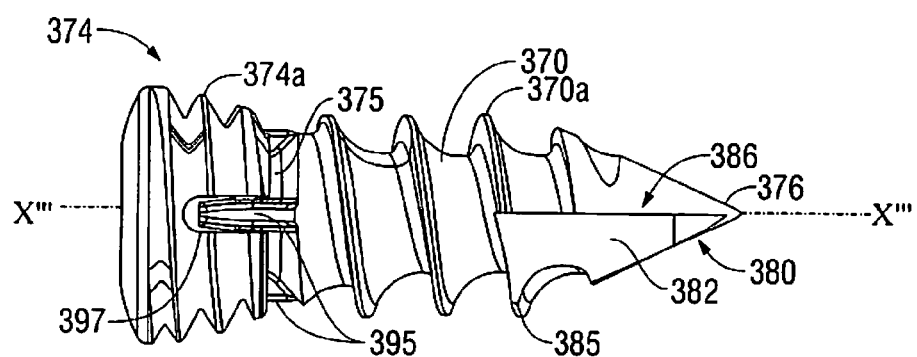

Referring now to FIGS. 9A and 9B, another embodiment of bone screw is shown referenced generally as 355. As described above with reference to bone screw 155, bone screw 355 is configured for use with spinal interbody spacer 100 and/or spinal interbody spacer 200 in the same manner as described hereinabove. Bone screw 355 includes a shank 370, a neck portion 375 extending between the shank 370 and a flange portion 390 disposed at a proximal end of neck portion 375, an independent tapered head portion 374, and a pointed tip portion 376 at a distal end of the shank 370. The shank 370 has a uniform outer diameter and a first continuous helical thread 370a formed thereon for threaded insertion into bone. A second continuous helical thread 374a is formed on the independent head portion for engaging lips 190b, 192b, 194b (FIG. 5) or lips 150a, 152a, 154a (FIG. 6) of spacers 100 and 200 respectively. The pitch of the first thread 370a is greater than the pitch of the second thread 374a. Each of the first and second threads 370a, 374a has a substantially uniform pitch.

Head portion 374 includes one or more slots 397 defined longitudinally therethrough and extending proximally from a distal end of head portion 374 through second thread 374a. A plurality of splines 395 are disposed along neck portion 375 and generally extend between a proximal end of first thread 370a and the longitudinal thickness of flange portion 390. Each slot 397 is configured to align with and receive a corresponding spline 395 to facilitate the mechanical coupling of head portion 374 to the proximal end of shank 370. More specifically, flange portion 390 is dimensioned such that as splines 395 advance through a corresponding slot 397, a distal end of head portion 374 expands to accommodate flange portion 390 therethrough and subsequently contracts circumferentially about neck portion 375, e.g., in an interface-fit manner, to mechanically couple head portion 374 to the proximal end of shank 370, as best shown in FIG. 9B. To facilitate expanding of the distal end of head portion 374, one or more stress-relief fissures (not explicitly shown) may be defined longitudinally through second thread 374a (i.e., parallel to slots 397). The independent head portion 374 configuration allows movement and/or rotation of the shank 370 about the "y" axis and "z" axis relative to the independent head portion 374 when the shank 370 and head portion 374 are mechanically coupled, as shown in FIG. 9B. Further, the independent head portion 374 configuration inhibits movement and/or rotation of the about the "x" axis. More specifically, the interaction between splines 395 and corresponding slots 397 inhibits movement and/or rotation of shank 370 about the "x" axis. As head portion 374 is engaged by a screw driver (not shown) to cause rotation of bone screw 355 in a clock-wise and/or counter clock-wise direction, the slots 397 defined through second thread 374a lockably engage corresponding splines 395 disposed along neck portion 375 to cause shank 370 to correspondingly rotate with head portion 374.

Bone screw 355 further includes a distal portion 380 that extends proximally from the pointed tip portion 376. In one embodiment, distal portion 380 may be configured such that bone screw 355 is a "self-starting" or "self drilling" bone screw. In other embodiments, distal portion 380 may be configured such that bone screw 355 is a "self-tapping" bone screw as discussed above with respect to bone screw 155. In either embodiment, distal portion 380 includes first and second sidewalls 382, 384 that define a flute section 386. As best shown in FIG. 9B by way of example, the first and second sidewalls 382, 384 of the flute section 386 extend from the pointed tip portion 376 to a crest 385 of thread 370a near the distal end of shank 370. The first sidewall 382 is planar and is aligned along a central longitudinal axis X'''-X''' of the bone screw 355 such that first sidewall 382 is coplanar with the central longitudinal axis X'''-X'''. As best shown in FIG. 9A by way of example, the second sidewall 384 further includes a planar portion 384a that is parallel to the central longitudinal axis X'''-X''' and an arcuate portion 384b that extends proximally from the planar portion 384a. The arcuate portion 384b is cut along a radius of curvature, as shown in FIG. 9A. Preferably, bone screws 355 are constructed of a material which is harder than the material of the lips 190b, 192b, 194b (FIG. 5) or lips 150a, 152a, 154a (FIG. 6). For example, the bone screw may be made of titanium alloy (e.g., Ti-6Al-4V) with the plate inserts or lips made of a softer compatible material, such as a softer titanium material.

Figure 10A:
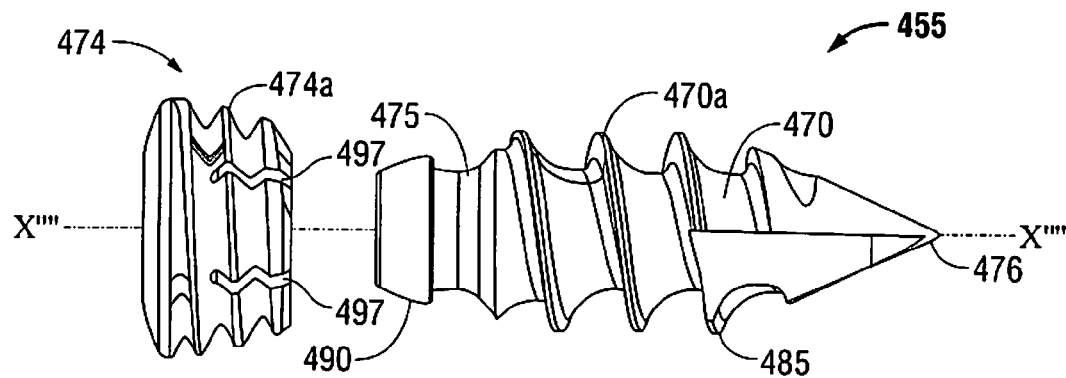
FIGS. 10A and 10B are side views of a bone screw for use with the spinal interbody spacers of FIGS. 1 and 6 according to another embodiment of the present disclosure.
Figure 10B:
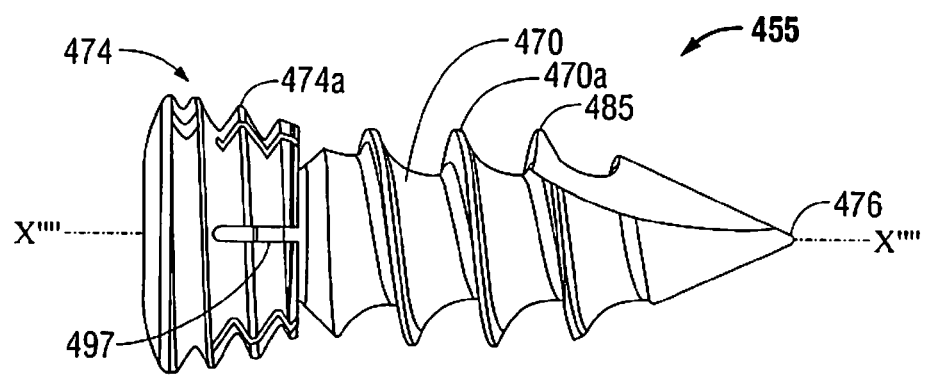

Referring now to FIGS. 10A and 10B, another embodiment of bone screw is shown referenced generally as 455. As described above with reference to bone screw 155, bone screw 455 is configured for use with spinal interbody spacer 100 and/or spinal interbody spacer 200 in the same manner as described hereinabove. Bone screw 455 includes a shank 470, a neck portion 475 extending between the shank 470 and a flange portion 490 disposed at a proximal end of neck portion 475, an independent tapered head portion 474, and a pointed tip portion 476 at a distal end of the shank 470. The shank 470 has a uniform outer diameter and a first continuous helical thread 470a formed thereon for threaded insertion into bone. A second continuous helical thread 474a is formed on the independent head portion for engaging lips 190b, 192b, 194b (FIG. 5) or lips 150a, 152a, 154a (FIG. 6). The pitch of the first thread 470a is greater than the pitch of the second thread 474a. Each of the first and second threads 470a, 474a has a substantially uniform pitch.

Head portion 474 includes one or more stress-relief fissures 497 defined longitudinally through second thread 474a and extending proximally from a distal end of head portion 474. Stress-relief fissures 497 operate to expand the distal end of head portion 474 to facilitate the mechanical coupling of head portion 474 to the proximal end of shank 470. More specifically, flange portion 490 is dimensioned such that as head portion 474 is mechanically coupled thereto, a distal end of head portion 474 expands to accommodate flange portion 490 therethrough and subsequently contracts circumferentially about neck portion 475, e.g., in an interface-fit manner, to mechanically couple head portion 474 to the proximal end of shank 470, as best shown in FIG. 10B. The independent head portion 474 configuration allows poly-axial movement (e.g., about 10°) of the shank 470 relative to the independent head portion 474 when the shank 470 and head portion 474 are mechanically coupled, as shown in FIG. 10B. Also, shank 470 is rotatable about the x axis.

Bone screw 455 further includes a distal portion 480 that extends proximally from the pointed tip portion 476. In one embodiment, distal portion 480 may be configured such that bone screw 455 is a "self-starting" or "self drilling" bone screw. In other embodiments, distal portion 480 may be configured such that bone screw 455 is a "self-tapping" bone screw. In either embodiment, distal portion 480 includes first and second sidewalls 482, 484 that define a flute section 486. As best shown in FIG. 10B by way of example, the first and second sidewalls 482, 484 of the flute section 486 extend from the pointed tip portion 476 to a crest 485 of thread 470a near the distal end of shank 470. The first sidewall 482 is planar and is aligned along a central longitudinal axis X""-X"" of the bone screw 455 such that first sidewall 482 is coplanar with the central longitudinal axis X""-X"". As best shown in FIG. 10A by way of example, the second sidewall 484 further includes a planar portion 484a that is parallel to the central longitudinal axis X""-X"" and an arcuate portion 484b that extends proximally from the planar portion 484a. The arcuate portion 484b is cut along a radius of curvature, as shown in FIG. 10A. Preferably, bone screws 455 are constructed of a material which is harder than the material of the lips 190b, 192b, 194b (FIG. 5) or lips 150a, 152a, 154a (FIG. 6). For example, the bone screw may be made of titanium alloy (e.g., Ti-6Al-4V) with the plate inserts or lips made of a softer compatible material, such as a softer titanium material.

Spinal interbody spacer 100 will now be described for use with bone screw 155. It should be understood that the following description is illustrative only in that spinal interbody spacer 100 or spinal interbody spacer 200 may be adapted for use with any one or more of bone screws 155, 255, 355, and 455. In the use of spinal interbody spacer 100, the body 102 is inserted between adjacent vertebrae such that protrusions 122 of top and bottom vertebral engaging surfaces 112a, 112b directly engage the surface of the adjacent vertebrae to prevent spinal interbody spacer 100 from dislodging from between the adjacent vertebrae. Once the body 102 of spinal interbody spacer 100 is inserted between adjacent vertebrae, bone screws 155 are advanced through screw openings 190a, 192a, 194a and corresponding apertures 150, 152, 154 toward hollow central region 134 such that self-starting portion 180 engages the adjacent vertebrae to threadingly advance thread shank 170 therein and anchor spinal interbody spacer 100 therebetween. As best shown in FIGS. 4 and 5 and as discussed hereinabove, aperture 150 is angled in a first direction and apertures 152 and 154 are angled in a second direction such that a bone screw 155 advanced through aperture 150 is configured to anchor spinal interbody spacer 100 to one of the adjacent vertebrae and bone screws 155 advanced through apertures 152 and 154 are configured to anchor spinal interbody spacer 100 to another of the adjacent vertebrae. As discussed hereinabove, as bone screw 155 is advanced through any one of apertures 150, 152, 154 toward hollow central region 134, thread 174a of head portion 174 engages the corresponding lip 190b, 192b or 194b to deform the lip and secure bone screw 155 in the corresponding screw opening 190a, 192a or 194a such that bone screw 155 resists backing out of the screw opening. Further, head portion 174 of bone screw 155 is dimensioned to engage lips 190b, 192b, 194b to prevent further advancement of bone screw 155 toward hollow central region 134.

With returned reference to FIGS. 9A and 9B, the independent head portion 374 configuration of bone screw 355 inhibits the backing out of bone screw 355 from apertures 150, 152, 154 (FIG. 5) or apertures 250, 252, 254 (FIG. 6). More specifically, the inhibition of movement and/or rotation of shank 370 about the "x" axis provided by the interaction between splines 395 and corresponding slots 397, inhibits corresponding rotation of head portion 374 about the "x" axis and, as a result, inhibits the dislodging and/or disengagement of the second thread 374a from lips 190b, 192b, 194b (FIG. 5) or lips 150a, 152a, 154a (FIG. 6).

It can be understood from the foregoing disclosure of the exemplary embodiment of spinal interbody spacer 100 that the spacer 100 provides a spinal implant that provides a desired amount of lordosis, and a desired spacing between adjacent vertebral bodies, resists movement once inserted, and provides a path for bone ingrowth.

It will be understood that various modifications may be made to the embodiments of the presently disclosed spinal interbody spacer. Therefore, the above description should not be construed as limiting, but merely as exemplifications of embodiments. Those skilled in the art will envision other modifications within the scope and spirit of the present disclosure. By way of example only, the preferred embodiment includes a PEEK interbody implant having titanium plate inserts to lock to the bone screws. It is contemplated that all or a portion of the implant itself could be made of titanium with the lips that lockingly engage the screws formed directly into the implant, rather than as a separate insert as shown.

What is claimed is:

1. A spinal spacer for engagement between vertebrae, comprising:
   a body having a first end surface at a distal end of the body and a second end surface opposite thereto at a proximal end of the body;
   the body extending between the first and second end surfaces to define opposing top and bottom vertebral engaging surfaces substantially symmetrical about a centerline axis, the body further defining side surfaces;
   a hollow inner body defined by an opening extending through the top and bottom vertebral engaging surfaces;

the second end surface of the body including at least one aperture formed therethrough at an angle relative to the centerline axis and in communication with the hollow inner body;

a bone screw having a threaded screw shaft configured and dimensioned to engage bone and a threaded screw head operably coupled to a proximal end of the screw shaft such that the threaded screw shaft is movable relative to the threaded screw head about at least one axis; and at least one insert having a screw opening defined therethrough and configured to be mounted to the body with the screw opening substantially aligned with the at least one aperture, the screw opening having a non-threaded lip formed therein, the non-threaded lip configured and dimensioned to engage the threads of the threaded screw head of the bone screw inserted through the at least one aperture.

2. The spinal spacer of claim 1, wherein the hollow inner body is further defined by an opening extending through the side surfaces.

3. The spinal spacer of claim 1, wherein the insert is metallic.

4. A spinal spacer for engagement between vertebrae, comprising:
a body having a first end surface at a distal end of the body and a second end surface opposite thereto at a proximal end of the body, the body extending between the first and second end surfaces to define opposing top and bottom surfaces, the body further defining side surfaces and a hollow open central region extending through the top and bottom vertebral engaging surfaces, the second end surface of the body including at least one aperture formed therethrough at an angle relative to a centerline axis extending between the proximal and distal surfaces, the at least one aperture configured to receive an insert therein, the insert having a screw opening defined therethrough and configured to align with the at least one aperture, the screw opening having a non-threaded lip formed therein, the non-threaded lip configured and dimensioned to engage threads on a head of a screw inserted through the at least one aperture, the head of the screw operably coupled to a threaded screw shaft that is movable relative to the head of the screw about at least one axis.

5. The spinal spacer of claim 4, further comprising a bone screw having a screw head and a screw shaft, the screw shaft having a thread thereon configured and dimensioned to engage bone and the screw head having thereon a screw thread configured and dimensioned to engage the lip of the screw opening.

6. The spinal spacer of claim 5, wherein the insert is made of a titanium material and the bone screw is formed of a titanium alloy material which has a hardness greater than the titanium material of the insert.

7. The spinal spacer of claim 4, further comprising a bone screw having a screw head configured to operably couple to a proximal end of a screw shaft, the screw shaft having a thread thereon configured and dimensioned to engage bone and the screw head having thereon a screw thread configured and dimensioned to engage the lip of the screw opening.

8. The spinal spacer of claim 7, wherein rotational movement of the screw head causes corresponding rotation of the screw shaft.

9. The spinal spacer of claim 7, wherein the screw head includes at least one slot defined therethrough configured to receive a corresponding spline disposed on the proximal end of the screw shaft to operably couple the screw head to the screw shaft.

10. The spinal spacer of claim 9, wherein rotation of the screw shaft about the x axis is inhibited.

11. The spinal spacer of claim 9, wherein movement away from the hollow open central region of the bone screw within the at least one screw opening is inhibited.

12. The spinal spacer of claim 7, wherein the screw head includes at least one stress-relief fissure defined therein and configured to permit momentary expanding of a distal end of the screw head and subsequent contraction thereof about the proximal end of the screw shaft to operably couple the screw head to the proximal end of the screw shaft.

13. The spinal spacer of claim 4, wherein the lip exists in a single plane that is substantially perpendicular to a longitudinal axis extending through the at least one aperture.

14. A spinal spacer for engagement between vertebrae, comprising:
a non-metallic body having a first end surface at a distal end of the body and a second end surface opposite thereto at a proximal end of the body, the body extending between the first and second end surfaces to define opposing top and bottom surfaces, the body further defining side surfaces and a hollow open central region extending through the top and bottom vertebral engaging surfaces, the second end surface of the body including at least one aperture formed therethrough, the at least one aperture having a body screw opening defined therethrough, the body further including a plate cavity; and at least one metal insert having an insert screw opening defined therethrough, the insert configured and dimensioned to be inserted into the plate cavity with the insert screw opening aligned with the body screw opening, the screw opening having a non-threaded lip formed therein, the non-threaded lip configured and dimensioned to engage threads on the head of a bone screw inserted through the at least one aperture, the head of the bone screw operably coupled to a threaded screw shaft that is movable relative to the head of the bone screw about at least one axis.

15. The spinal spacer according to claim 14, further comprising a bone screw having a screw head and a screw shaft, the screw shaft having a thread thereon configured and dimensioned to engage bone and the screw head having thereon a screw thread configured and dimensioned to engage the lip of the screw opening.

16. The spinal spacer according to claim 15, wherein the screw head is configured to operably couple to a proximal end of the screw shaft.

17. The spinal spacer of claim 15, wherein the metal insert is made of a titanium material and the bone screw is formed of a titanium alloy material which has a hardness greater than the titanium material of the metal insert.

18. The spinal spacer according to claim 14, wherein the at least one aperture is at an angle relative to a centerline axis extending between the proximal and distal surfaces of the body.

19. A method of fusing adjacent vertebrae, comprising:
inserting a spinal spacer between the surfaces of the adjacent vertebrae, the spinal spacer extending between a first end surface at a distal end and a second end surface at a proximal end to define opposing top and bottom surfaces substantially symmetrical about a centerline axis, the second end surface having at least one angled aperture defined therethrough and at least one corresponding plate insert having a screw opening configured to substantially align with the at least one angled aperture; and advancing a bone screw through a first angled aperture defined through the second end surface of the spinal spacer at a first angle relative to the centerline axis and into the vertebrae until the bone screw engages bone and threads on the head of the bone screw engage a non-threaded lip formed in the screw opening to secure the bone screw relative to the spinal spacer the head of the bone screw operably coupled to a threaded screw shaft such that the threaded screw shaft is movable relative to the head of the bone screw about at least one axis.

20. The method of claim 19, wherein the second end surface includes at least a second angled aperture defined therethrough and at least one corresponding plate insert having a screw opening configured to substantially align with the at least one aperture.

21. The method of claim 19, further comprising advancing a second bone screw through the second angled aperture.

22. The method of claim 21, wherein the second angled aperture is defined through the second end surface of the spinal spacer at a second angle relative to the centerline axis.

23. A method of fusing adjacent vertebrae, comprising:
inserting a spinal spacer between the surfaces of the adjacent vertebrae, the spinal spacer extending between a first end surface at a distal end and a second end surface at a proximal end to define opposing top and bottom surfaces substantially symmetrical about a centerline axis, the second end surface of the body including at least one aperture formed therethrough at an angle relative to a centerline axis extending between the proximal and distal surfaces, the at least one aperture having a metal insert disposed therein, the metal insert having a screw opening defined therethrough configured to align with the at least one aperture; and advancing a bone screw through a first aperture defined through the second end surface of the spinal spacer at a first angle relative to the centerline axis and into the vertebrae until the bone screw engages bone and threads on the head of the bone screw engages a non-threaded lip formed in the screw opening to secure the bone screw relative to the spinal spacer, the head of the bone screw operably coupled to a threaded screw shaft that is movable relative to the head of the bone screw about at least one axis.

24. The method of claim 23, wherein the second end surface includes at least a second aperture defined therethrough and at least one corresponding screw opening, the second aperture being defined at a second angle relative to the centerline axis.

25. The method of claim 24, further comprising advancing a second bone screw through the second aperture.

26. A spinal device comprising:
a non-metallic body having an anterior wall, a posterior wall, and opposing side walls, the side walls extending between the anterior wall and the posterior wall;
at least one opening extending through the body;
an aperture disposed on the posterior wall; and
a metal insert having a screw opening, the insert configured and dimensioned for placement within the aperture such that the screw opening is aligned with the at least one aperture, the screw opening having a non-threaded lip formed therein, the non-threaded lip configured and dimensioned to engage threads on the head of a screw inserted through the aperture, the head of the screw operably coupled to a threaded screw shaft that is movable relative to the head of the screw about at least one axis.

27. The spinal device of claim 26, wherein the insert is releasably positioned within the aperture.

28. The spinal device of claim 26, wherein the body further includes a top surface and a bottom surface, the top and bottom surfaces having a plurality of protrusions extending therefrom.

29. The spinal device of claim 28, wherein the at least one opening extends between the top and bottom surfaces.

30. A spinal spacer for engagement between vertebrae, comprising:
a body having a first end surface at a distal end of the body and a second end surface opposite thereto at a proximal end of the body, the body extending between the first and second end surfaces to define opposing top and bottom surfaces,
the body further defining side surfaces and a hollow open central region extending through the top and bottom vertebral engaging surfaces, the second end surface of the body including at least one aperture formed therethrough at an angle relative to a centerline axis extending between the proximal and distal surfaces,
the at least one aperture having a screw opening defined therethrough, the screw opening having a lip formed therein; and
a bone screw having a screw head configured to operably couple to a proximal end of a screw shaft, the screw shaft having a thread thereon configured and dimensioned to engage bone and an outer surface of the screw head having thereon a plurality of screw threads configured and dimensioned to engage the lip of the at least one aperture, wherein the screw head includes at least one stress-relief fissure defined therein and configured to permit momentary expansion of a distal end of the screw head and subsequent contraction thereof about the proximal end of the screw shaft to operably couple the screw head to the proximal end of the screw shaft.

31. A spinal spacer for engagement between vertebrae, comprising:
a body having a first end surface at a distal end of the body and a second end surface opposite thereto at a proximal end of the body, the body extending between the first and second end surfaces to define opposing top and bottom surfaces, the body further defining side surfaces and a hollow open central region extending through the top and bottom vertebral engaging surfaces, the second end surface of the body including at least one aperture formed therethrough at an angle relative to a centerline axis extending between the proximal and distal surfaces, the at least one aperture configured to receive an insert therein, the insert having a screw opening defined therethrough and configured to align with the at least one aperture, the screw opening having a lip formed therein, the lip configured and dimensioned to engage threads on a head of a screw inserted through the at least one aperture; and
a bone screw having a screw head configured to operably couple to a proximal end of a screw shaft, the screw shaft having a thread thereon configured and dimensioned to engage bone and the screw head having thereon a screw thread configured and dimensioned to engage the lip of the screw opening, wherein the screw head includes at least one stress-relief fissure defined therein and configured to permit momentary expanding of a distal end of the screw head and subsequent contraction thereof about the proximal end of the screw shaft to operably couple the screw head to the proximal end of the screw shaft.

32. The spinal spacer of claim 31, wherein the lip exists in a single plane that is substantially perpendicular to a longitudinal axis extending through the at least one aperture.

33. A spinal spacer for engagement between vertebrae, comprising:

a body having a first end surface at a distal end of the body and a second end surface opposite thereto at a proximal end of the body, the body extending between the first and second end surfaces to define opposing top and bottom surfaces, the body further defining side surfaces and a hollow open central region extending through the top and bottom vertebral engaging surfaces, the second end surface of the body including at least one aperture formed therethrough at an angle relative to a centerline axis extending between the proximal and distal surfaces, the at least one aperture having a screw opening defined therethrough, the screw opening having a non-threaded lip formed therein; and a bone screw having a screw head configured to operably couple to a proximal end of a screw shaft such that the screw shaft is movable relative to the screw head about at least one axis, the screw shaft having a thread thereon configured and dimensioned to engage bone and an outer surface of the screw head having thereon a screw thread configured and dimensioned to engage the non-threaded lip of the screw opening such that the thread on the outer surface of the screw head deforms the non-threaded lip to secure the bone screw relative to the screw opening.

34. The spinal spacer of claim 33, wherein the non-threaded lip is made of a titanium material and the bone screw is formed of a titanium alloy material which has a hardness greater than the titanium material of the non-threaded lip.

* * * * *